United States Patent [19]

Smith

[11] Patent Number: 5,869,540
[45] Date of Patent: Feb. 9, 1999

[54] HERBAL TREATMENTS FOR IMPROVING SKIN APPEARANCE

[76] Inventor: Walter P. Smith, 46 Wakeman Rd., New Canaan, Conn. 06840

[21] Appl. No.: 625,751

[22] Filed: Mar. 29, 1996

[51] Int. Cl.$^6$ ............................. A01N 25/00; A61K 47/00
[52] U.S. Cl. ...................................... 514/783; 424/195.1
[58] Field of Search .......................... 514/783; 424/195.1

[56] References Cited

U.S. PATENT DOCUMENTS 5,578,312  11/1996  Parrinello ................................ 424/401

*Primary Examiner*—Shelley A. Dodson
*Assistant Examiner*—Michael A. Williamson
*Attorney, Agent, or Firm*—Handal & Morofsky

[57] ABSTRACT

The invention provides herbal treatments for aged skin employing valerian extracts and other active herbal agents that are effective as relaxants. Surprisingly, mere ingestion of valerian tea on a daily basis is effective to reduce deep wrinkles. The treatments are particularly effective on persons afflicted by stress and are shown by clinical tests to reduce wrinkles and acne lesions and to improve skin texture and skin color without an increase in puffiness such as might be expected from mere hydration of the skin. The herbal agents can be administered either in a tea or a topical composition, and a combination of the two treatments is particularly effective. A preferred herbal agent is an aqueous valerian root extract. Other herbal agents include extracts of passion flower and mullein.

17 Claims, No Drawings

HERBAL TREATMENTS FOR IMPROVING SKIN APPEARANCE

TECHNICAL FIELD

The present invention relates to novel herbal treatments for improving the appearance of unadorned skin, especially aged or deeply wrinkled skin. The treatments of the invention are novel herbal treatments that are effective to change the visual appearance of the skin itself when observed in an unadorned condition. In other words, the inventive treatments are not cosmetic treatments which provide opaque films to mask and alter the superficial appearance of the skin while leaving the naked skin unchanged, but rather are active treatments which induce biological changes that improve the skin's appearance. Some examples of agents used in such active treatments are alpha hydroxy acids and retinoids. Though they are not per se cosmetic masking treatments, the invention does provide, in one aspect, topical treatments that can be formulated into a wide range of cosmetics.

More particularly, the invention provides proactive treatments such that the skin has a better appearance as a result of the treatment than it had before application of the treatment. A proactive treatment is to be distinguished from a prophylactic treatment which merely opposes or prevents some undesired effect occurring, as for example, when a sun screen protects against skin damage from ultraviolet rays. Although the treatments the invention provides may also, in some cases, be effective for treatment of disease conditions or skin abnormalities, treatments according to the invention are intended for improving normal, albeit aged, skin, especially to reduce, or reduce the appearance of, deep wrinkles. The invention provides proactive herbal treatments, employing complex biologically derived, plant source materials, that have beneficial effects on the appearance of unadorned skin.

BACKGROUND

As skin ages it loses its attractive youthful appearance. Aging may be simple chronological passing of the years or photoaging induced by exposure to the sun. Wind, rain or other environmental stresses can cause or aggravate declines due to aging. With aging smooth, firm, clear, attractively colored skin can develop wrinkles, fine lines, flaccid texture, acne lesions, puffiness and poor color. These negative effects tend to congregate around the eyes and are particularly noticeable in the eye area, which is the focal point of a person's appearance.

Many people, especially women, wish to ward off the visual effects of aging, if only superficially. This desire has spawned the use of the cosmetics to modify the appearance of the skin since ancient times, and has led to the creation of a vast industry in modern times. Most cosmetics, for example foundation, blusher, eye shadow and lipstick, provide an opaque film which is overlaid on the skin to display the film's own visual characteristics or to enhance those of the underlying skin. However the benefits of opaque, masking or film-forming cosmetics are transitory and limited or artificial in effect. Accordingly, there is a need for skin treatments that provide more durable, natural and substantial effects.

Some cosmetic treatments actually induce biological changes in the skin. Perhaps if they were used sufficiently diligently, ancient treatments employing yogurt, fruit acids or vinegar may have ben effective to induce such changes because these natural sources contain simple alpha hydroxy acids which are now known to be quite effective in inducing structural changes in the skin and are widely incorporated in commercial cosmetic and therapeutic treatments and treatment compositions.

Also, many people shun the achievements of modern science and cosmetology and prefer herbal treatments perceiving them to be more natural and more desirable. A number of successful present-day beauty treatments and lines of cosmetics are promoted for their plant-origin ingredients, although often such products contain little in the way of active ingredients obtained from plants. In many cases, the supposed activity of the plant-origin ingredients is unsubstantiated. However there are efficacious herbs with useful properties for cosmetic applications.

There is a rich lode of knowledge of herbal treatments, much compiled also in ancient times, by the Chinese, Indians, Africans, American Indians and indeed probably most ancient cultures, and most people, even scientists, recognize that at least some herbal remedies have genuine therapeutic value. Nowadays modern drug companies are focusing increased resources on research into therapeutic agents derived from plant sources, as more traditional synthetic organic chemistry research provides diminishing returns. In medicine a famous, effective drug derived from plant sources is the anti-malarial agent quinine. More modern successful plant-derived drugs include the cardiac drug digitalis, which is isolated from the foxglove plant and the anti-cancer agents visblastine and vincristine, both isolated from periwinkle. Current research efforts are finding interesting potential anti-cancer properties to be exhibited by tasol an experimental drug isolated from the Pacific yew and certain polyphenols isolated from Chinese green tea.

The efficacy of a number of herbal remedies has been demonstrated in clinical trails or animals studies. For example, chamomile has been shown to be effective against inflammation and spasms in the digestive tract. Echinacea has a mild stimulatory effect on the immune system. Feverfew can apparently relieve migraine pain and is used to prevent migraine and for arthritic, menstrual irregularities, stomach ache and fever. Clinical studies also support an ability of garlic to lower cholesterol. Laboratory finding suggest ginger and peppermint can help stave off or fight colds, and there is some evidence to back claims for the digestive properties of peppermint. Gingko is apparently effective for brain-related mild disorders such as short-term memory loss, headache and depression as well as tinnitus. Goldenseal is widely used in a tea for eye inflammations and for respiratory conditions and has been shown in animal studies to be effective against a number of microorganisms, but may have some mild toxicity.

Milk thistle has been shown effective in treating liver conditions and is so approved in Germany. Valerian is also approved in Germany as a mild tranquilizer for restlessness and sleep disturbances. Willow bark is traditionally used in a tea for headache, fever, muscle pain and arthritis and the presence of salicylates in willow bark is consistent with such used, but the concentration of active ingredients may be too low for it to be an effective medication. Much of this data is reported in "Health" magazine May/June 1995, pages 86–92.

Some herbs, or plant-derived biological materials, have bene used to treat the skin, and may, or may not improve its appearance. For example, aloe and Malvaceae extract (Hibiscus lipids) have been used as moisturizers; licorice (β-glyceritinate) and rosemary as anti-irritants; and extracts of queen-of-the-meadow and willow bark have been promoted as having anti-aging properties believed attributable to their content of salicylic acid.

Other plants are known whose extracts may have useful topical anti-aging properties. For example, *Centella asiatica* contains asiatic acid which is believed to stimulate collagen synthesis and heather extracts are used as inhibitors of elastic breakdown.

Many of these herbal treatments are popular and commercialized in European and other countries outside the United States where drug regulatory bodies are generally more receptive to drugs derived from natural products than they are in the U.S.A.

Some herbal technology has reached the patent literature, for example at least 50 U.S. patents reference garlic in their abstracts or titles, and at least four reference chamomile.

U.S. Pat. No. 5,211,948 to Cerise et al. discloses a manufacturing method for producing a powdered concentrated extract of valerian. U.S. Pat. No. 5,248,503 discloses an herbal dietary supplement comprising a solution of at least two herbal ingredients selected from a wide-ranging list which is allegedly holistically effective for treatment of multiple complaints especially oral complaints such as cold sores and oral boils, pimples and acne, employing a treatment medium in a variety of forms including a cream. To the extent that it applies to the application of a cream to pimples or acne, patent '502 apparently discloses a topically applied herbal treatment. However, patent '503 teaches nothing about improving the appearance of unadorned aged skin.

U.S. Pat. No. 5,407,677 to Toiminaga et al. discloses an herbal gel composition containing inter alia fennel extract intended to be applied to the skin to increase lipase activity and thus accelerate lipid metabolism. The purpose of the treatment is apparently to reduce excess or undesired subcutaneous fat. Again, although patent '677 discloses a topically applied herbal treatment, there is no teaching regarding improving the appearance of aged skin nor does it suggest any treatment for reducing wrinkles.

Bonne et al. U.S. Pat. No. 4,749,573 discloses a cosmetic composition for topical application containing an extract of the fruits of *Silybum marianum*, common name "milk thistle". The treatments disclosed are reported to be effective in opposing aging of the skin. More specifically, they apparently protect against free radical damage in animal and in vitro studies. Thus the Bonne's treatments are prophylactic not proactive. Bonne does not teach any treatment that will improve the appearance of skin that has already aged: Bonne's objective is to prevent photoaging occurring.

None of these patents teaches a herbal treatment that significantly reduces the signs of aging of the skin or that is effective in treating wrinkles, especially deep wrinkles. As used herein, the term "deep wrinkles" (or "deeply wrinkled") refers to wrinkles with a depth of at least 1 mm, that involve, or are controlled or influenced by the musculature, and distinguishes from fine, superficial wrinkles that can be relatively easily removed or concealed.

Though not regarded as herbal ingredients, alpha hydroxy acids are known to be effective in stimulating skin renewal thereby improving the appearance of aged skin, and of wrinkles in the aged skin even although the wrinkles may still be present. Yu and Van Scott in U.S. Pat. No. 5,422,370 claim a method of reducing wrinkles by topical application of latic acid to the wrinkle. Alpha hydroxy acids are believed to work via epidermal stimulation and, accordingly only small or superficial wrinkles are susceptible to reduction by alpha hydroxy acids. Deep, muscle-controlled wrinkles are non-superficial and although they may be less noticeable because their skin surface is smoother.

To solve this problem, some plastic surgeons are known to have injected botulism toxin into facial muscles to improve the look of the skin immediately. The botulism toxin paralyses the muscle receiving it and in doing so the deep wrinkles controlled by the muscle become relaxed. There are obvious drawbacks to this procedure. It does not produce long-term effects, employs toxins, and cannot be performed regularly.

Psychologists report, anecdotally, that the side of the face controlled by the harder working side of the brain becomes wrinkled the more readily. Such reports are consistent with long-held anecdotal associations of wrinkles with anxiety. Though interesting, this knowledge does not suggest an effective treatment for deep wrinkles that can be commercialized.

Many or most of the known skin treatments are topical in nature, requiring to be spread on, or rubbed into, all areas of the skin to be treated. Topical applications of creams, gels or lotions may be acceptable, or agreeable, for many users, but others may find them tiresome or disagreeable, especially if many areas of the body are to be treated repeatedly. A herbal deep wrinkle treatment which also solved the problem of repeated topical application would be particularly desirable.

SUMMARY OF THE INVENTION

The invention, as claimed, is intended to provide a remedy. It solves the problem of providing an effective herbal treatment capable of reducing deep wrinkles in the skin.

Accordingly, the invention provides a herbal treatment for deep wrinkles comprising chronic oral administration for at least two weeks of a beverage containing an amount sufficient of a valerian root extract to provide a desired reduction in the appearance of said deep wrinkles. The chronic oral administration can be effected by an individual, particularly, but not exclusively, an individual suffering from stress-induced muscular tension, drinking at least two 100 ml. aliquots per day of valerian tea at least twice daily for at least four weeks until a desired improvement in the deep wrinkles is obtained. Preferably, each aliquot of valerian tea contains an aqueous extract of from about 0.1 to about 2 g. of powdered valerian root.

As verified by clinical studies reported herein, valerian can improve the skin's appearance to a surprising degree. It is also surprising that such an improvement can be obtained from a simple, palatable drink taken as described herein, that significant results are quickly obtained and that a long-term chronic cumulative benefit is observed.

Test data described hereinbelow shows that valerian tea alone can reduce deep wrinkles quite rapidly, apparently by relaxing the individual and reducing the muscle tension that controls or influences the deep wrinkles. Significant results are detectable after only two weeks, in many cases, which is much quicker than the periods of 8–12 weeks, or more, that are required by conventional wrinkle treatments such as alpha hydroxy acids or retinoids.

A significant surprise is that when valerian tea is used chronically for 4 to 8 or more weeks, an enduring improvement can be observed that may continue long after valerian tea treatments are discontinued. It appears that by relaxing the tissue over a period of time, the skin is repairing itself, undoing damage that has been done over the years. When a skin repair agent, such as a skin acid, for example an alpha hydroxy acid or retinoid, is used in combination with the valerian tea improvements can be obtained more rapidly.

In another aspect, the invention comprises topical application to the wrinkles to be reduced of a topical composition comprising an effective amount of an aqueous valerian extract. Another surprise is that a valerian root extract can be effective on wrinkles when applied in a topical composition, for example a cosmetic gel. Such topical application of valerian root extract apparently does not plump out the skin via hydration, does not increase cell renewal, doe snot immediately reduce fine lines but over time reduces deeper lines and wrinkles that may be associated with or due to muscle contraction or other muscle behavior or deep tissue phenomenon. Thus, the valerian root extract appears to be capable of exerting beneficial effects topically.

Oral administration or tea drinking can be combined with a topical application for enhanced results. Surprising the effects are commulative and seem to be more or less permanent apparently due to a re-structuring of the skin.

The inventive treatments can also be combined with topical application of an alpha hydroxy acid for more pronounced results, working on fine lines and similar superficial blemishes to give an enhanced overall cosmetic effect.

Use of a valerian tea infusion pursuant to the invention apparently relaxes the individual, provides an immediate visual improvement in deep wrinkles and when continued, allows the skin to repair itself.

Use of a topical cream or gel containing a valerian root extract over time targets its action to areas that need it and apparently improves deep wrinkles by relaxing muscles that, as it were, lock in wrinkles, leading to tissue structures in which the dermis has become folded and collagen layers and the like have been deformed. A valerian or other relaxant herbal cream or gel according to the invention can remove the deformation. Topical compositions are valuable for any individual who does not want to be relaxed by systemic ingestion of valerian enabling them to obtain wrinkle-reducing benefits, albeit more slowly.

In a further aspect, the invention provides a herbal skin treatment for improving the appearance of aged skin comprising administering a skin treatment composition containing an effective quantity of a biologically active relaxant herbal agent to a subject having visually apparent aged skin, for a period of time sufficient to obtain a desired improvement. Preferably, the treatment is administered daily for at least two weeks to subjects suffering from stress-induced tension.

Preferably also the herbal agent has relaxant properties, is substantially non-toxic, can be satisfactorily formulated for administration and is selected from the group of herbal agents having muscle-relaxant, anti-hypertensive, anti-convulsant or tranquilizing properties. It can be selected from the group comprising valerian, passion flower and mussein extract.

One preferred treatment comprises an orally ingestible potable tea or hot water infusion of a plant material, or concentrated extract of plant material, providing a suitable source of the active herbal agent. The treatment may comprise a cosmetic composition formulated with cosmetic excipients for topical application.

The invention also provides a combined treatment comprising a combination of the ingestion of a herbal tea containing an effective amount of a first relaxant herbal agent and the daily topical application of a cosmetic composition also containing an effective amount of an active herbal relaxant agent. Preferably, the active herbal relaxant agent in both the tea and the cosmetic composition is an extract of a herb selected from the group consisting of valerian, passion flower and mullein.

A particularly preferred herb is valerian, known to the gardener and horticulturalist in the species "heliotrope". Extracts of other herbs having muscle-relaxant, anti-hypertensive, anti-convulsant or tranquilizing properties can also be used, for example passion flower, mullein, skullcap, lady's slipper (*cypriperdium pubescens*), magnolia, arrach (*chenopodium olidum*) and Pinella.

Although the herbal treatments of this invention can be used by anyone desiring to improve the appearance of aged skin, and are believed to be beneficial to all types of appearance-marred aged skin, the invention is particularly applicable to treating the skin of individuals afflicted with stress-induced muscle tension, or clinically overstressed individuals, and can provide beneficial results which are difficult to obtain in other ways.

Alternatively, where stress-inducing factors are unavoidable or difficult to remove, many people may simply prefer to use the effective treatments of the invention rather than traditional stress-reducing drugs or medications, simply because the inventive treatments are herbal in nature. As will be apparent, the inventions orally ingestible teas and topical treatments are not masking cosmetics providing merely transient improvements in skin appearance, but provide long-lasting condition or structural improvements.

The treatment can be administered in various forms, as are well known for herbal remedies and cosmetic application, but a preferred formulation is at a tea or hot water infusion of a plant material or concentrated extract providing a suitable source of the active herb. Herbal teas are a popular and soothing beverage when ingested warm or hot and, are refreshing in the hot days of summer. Herbal treatments according to the invention can also be cosmetic compositions intended for topical application, using conventional cosmetic excipients. A particularly effective treatment employs a combination of the ingestion of herbal tea containing an effective amount of a first relaxant herbal agent accompanied by the topical application of a cosmetic composition containing an effective amount of a further active herbal relaxant agent which is preferably the same as the first, but may be a different agent, if desired.

Clinical tests 1 have conducted using valerian and passion flower as active herbal relaxant agents, against appropriate controls, have shown that undesired aged skin characteristics such as wrinkles, acne lesions, and puffiness are significantly reduced by the ingestion of valerian root tea and this reduction attains a surprising intensity when ingestion of the tea is accompanied by topical application of a cream containing valerian. Also, desirable skin texture and skin color characteristics are enhanced. These tests and their results are described further hereinbelow.

I have observed that the appearance of aged skin is adversely affected by stress-induced tension. I have further observed that traditional medical treatments for stress, or lifestyle changes to eliminate stress-inducing factors improve the appearance of aged skin. These improvements are relatively modest and more significant results are obtained by the herbal treatments of the invention described herein, especially when combined ingestion therapy is combined with a topical treatment and used over a protracted period of time.

DETAILED DESCRIPTION OF THE PREFERRED EMBODIMENTS

Overview

Among the many abnormalities to which the skin is subject as it ages, wrinkles are particularly problematic, being visually prominent and difficult to eradicate. Fine lines are less troublesome and respond well to treatments such as hydration and alpha hydroxy acids. Muscle behavior and condition are frequently involved in the phenomenon of deep wrinkles, which for convenience can be defined as being in excess of 1 mm deep, (although somewhat less deep wrinkles may have equivalent properties) and the described conventional treatments that are effective for fine lines have little impact on the musculature controlling or involved with such deep wrinkles. Tension in some muscles, causing them to remain in a contracted condition, coupled with loss of firmness and weakness in opposing muscles, can lead to the folding and deep lining of the skin which is characteristic of wrinkles.

The herbal treatments of this invention solve this problems and improve deep wrinkles. In doing so, the inventive herbal treatments apparently act on the wrinkle-involved musculature to improve its condition. Specifically, the treatments apparently act to relax tensed muscles, that have become, as it were set in a contracted condition, enabling weaker opposing muscles to smooth relevant wrinkling.

While other herbs are known or will be identified that are suitable sources for the active herbal relaxing agent used in the treatments of this invention, as stated above, a preferred herb which I have found to be particularly and surprisingly effective in improving the unadorned appearance of aged skin, is valerian.

Valerian

Valerian is a popular, widely used herb that has been known since ancient times as a relaxant with antispasmodic and calmative properties. Valerian has been approved in Germany for restlessness and for sleep disturbances.

According to "The Herb companion" February/March 1995 pages 28–29 valerian is a mild sedative which acts by depression of the central nervous system and by relaxation of smooth muscle tissue, which properties have been confirmed by scientific studies. Other uses which probably hail from ancient times are as a diuretic, menstrual aid and anti-epileptic. Valerian root or root extract has reportedly been recommended for use as a tea or as a poultice for relief of painful rheumatic or swollen joints. It has been used to treat dandruff, coughs, constipation, cholera and flatulence, and was esteemed in medieval times as "all-heal". Also described as a stimulant or nerve tonic. Cats and rats are attracted to the bruised or exposed roots. Overdoses of valerian may cause headache, vomiting, muscular spasms, dizziness and depression. Valerian is generally recognized as safe as a flavoring for candy desserts baked foods, beverages and meat products.

New Webster's Dictionary of the English Language, Delair Publishing Co., Inc. 1971–1981 defines valerian as "Any of the perennial herbs constituting the genus Valeriana as *V. Officinalis*, the garden heliotrope, a plant with white or pink flower and a root yielding a drug formerly used as a nerve sedative and an agent to check spasms; the drug obtained from the root of valerian official;". Noting that the term "valerian" is commonly used for a variety of plants not members of the genus Valeriana, the term "valerian" is used herein in the sense of Webster's, noting also that the invention selects for its treatments those valerian plants or plant extracts that have medicinal relaxant properties. Plants that are not members of the genus Valeriana are not included within the term "valerian". However, if they possess appropriate herbal relaxant properties, they can be used in the practice of this invention.

Various species of valerian are easily grown and widely naturalized plants, especially in wet areas throughout Europe much of North America, western Asia and Africa. Not unattractive with their light ferny appearance, its erect hollow grooved stems are typically from two to five feet tall and bear fluffy two to four inch clusters of small fragrant white, pink or lavender flowers that bloom in mid-summer. The basal leaves are ovate and deeply lobed while the paired dark green stem leaves are pinnately divided into five to twelve pairs of toothed leaves that become smaller toward the top of the stem. The flower's fragrance resembles that of haliotrope, a member of the borage family. Other parts of the valerian plant have a musky odor, which grows in more offensive on drying, thence the ancient name "phu" since commemorated in the species.

Valerian is commercially available in a number of forms, as the dried root, or dried and powdered root, as a juice as an extract, and as small pills. Aqueous extracts of valerian roots are also available. Any of these forms of valerian can be used in the practice of the present invention. Furthermore, the valerian powder described in Cerise et al. U.S. Pat. No. 5,211,948 appears to be suitable for use in the practice of the invention. In the Cerise patent an aqueous extract of valerian root is concentrated to eliminate volatile odors and insolubles are precipitated with alcohols or acetone and the refined extract is dried to a powder using a carbohydrate. This technique appears to retain a broadband spectrum of aqueous solubles suitable for use in the practice of this invention. Any material from a suitable valerian plant having activity providing relaxant properties can be used to provide a herbal agent useful in the practice of this invention, but the root is generally regarded as the best source of active herbal agents.

A particularly preferred raw material is pulverized or powdered valerian either purified as per the Cerise et al patent, or other known or readily devised methods, or in the crude state. This powder is readily brewed with hot water and, although it is somewhat bitter in taste, the palatability of the resultant infusion can be enhanced by the addition of suitable flavorants.

Formulation of Teas With a Relaxant Herbal Active

Hot and cold teas, prepared by infusing or steeping herbs have long been employed by herbalists and herb users. The traditional methods of employing teas and traditional teachings regarding the herbal strength of such teas are appropriate to the practice of the present invention in its selection of herbs containing an active relaxant for treatment of visually degraded or deteriorated skin.

EXAMPLE 1

Preparation of a Valerian Tea

A potable valerian infusion is prepared using a conventional decaffeinated ordinary tea made from the tea plant, (for example, using LIPTON, trademark, tea leaves) brewed with hot water to be dilute, or weak, with the addition of about 1 g. of pulverized or powdered, dried valerian root per 100 ml. of tea to the conventional dried tea leaves. The resultant brew is allowed to steep for about 3–5 minutes, and the particulates are filtered out providing an infusion ready for ingestion, after cooling, if necessary. The decaffeinated ordinary tea serves to make the recipe more potable.

Other caffeine-free tea-plant teas from other suppliers can be used as can inert caffeine-free teas from other plants sources, for example, chamomile, to improve the palatability of the valerian brew, or the valerian brew can be flavored with honey, lemon, sugar, or the like, or some people may prefer to imbibe it unflavored.

Individuals suffering stress-induced tension drinking at least two 100 ml. aliquots or cups per day of valerian tea prepared according to Example 1, on a daily basis for a period of at least two weeks, preferably with from about 6 to about 12 hours between cups, can provide improvement in the appearance of aged or deteriorated skin, as described herein, and may be continued until a desired improvement is obtained.

Relative Proportions of Ingredients

Teas. As just described, daily drinking of two cups of valerian tea, each containing the hot water extracts of about 1 g. of powdered valerian root are effective to provide the benefits of the invention, and this intake is contemplated as preferably for women of average height, about 63 inches. Both the strength of the valerian tea and the total daily uptake of valerian extract may be varied while providing the benefits of the invention, was will be apparent to those skilled in the art.

Increasing the strength of the tea beyond about 2 g. powdered valerian root per 100 ml. of tea is likely to provide an unpotable, excessively bitter brew, while a concentration of at least 0.1 g, more preferably at least 0.5 g. powdered valerian root per 100 ml. of tea is preferred for adequate potency. As an alternative to powdered root, an extract with hot water, or for topical compositions, with an aqueous solvent mixture, in equivalent proportions, can be used.

Topical Compositions. As stated above, the invention embraces the use of topical compositions containing an effective amount of valerian extract, used alone, or in combination with ingestion of tea, to improve the appearance of aged skin and in particular to reduce the visibility of deep wrinkles. To formulate valerian extracts in topical compositions, notably cosmetic or medicament compositions, such as gels., lotions, creams or liquids, some knowledge of the potency or efficacy of typical valerian extracts for the purposes of the present invention, is helpful in determining an effective amount or effective concentration of extract. In vitro growth stimulation of fibroblast cultures was used to calibrate valerian extracts for potency.

According to this test, a valerian root fraction extracted with hot water at a concentration of 10 g. dry powdered Valerian root per 100 ml. ("10% extract") showed very good responses, plateauing at about a 5 percent by weight concentration of the extract further diluted with water with useful activity in the range of about 1 to about 5 percent concentration of the extract in water. Based on this information, effective porportions of a 10% valerian root extract for employment in topical compositions is possibly from about 0.5 to about 10 percent by weight of the composition although from about 1 to about 7 percent is preferred, and from about 3 to about 5 percent is more preferred. Commercially, it would appear to be wasteful to use a concentration in excess of about 10 percent, although up to about 15 percent might be used, and indeed, as stated, lower ranges appear to be preferable at this time. However, for test purposes, in clinical studies such as described hereinbelow, because of the difficulty and expense of conducting a large number of in vivo bracketing trials to determine optimum effective amounts and concentrations, as one might were in vitro studies alone deemed adequate, a relatively high concentration of valerian root extract in topical compositions of about 10 percent can be used.

Other extraction solvents or solvent mixtures than hot water may be used, for example, water with up to about 20% ethyl or isopropyl, or n-propyl alcohol, optionally with from about 10 to about 20 percent propylene or butylene glycol.

Optional Ingredients

Some useful optional additional ingredients that can be incorporated individually or in combination one with another, in topical compositions employed in the invention include conventional cosmetic ingredients that enhance the properties of the formulation including, for example, emollients, fragrances, colorants and the like.

Active ingredients that provide supplementary structural skin improvements can be used, for example, skin renewal stimulating acids such as alpha hydroxy acids, or retinoids, in quantities known to be effective, can reduce fine, or superficial wrinkles, as well as fine lines and other minor skin blemishes.

The presence of naturally occurring alpha hydroxy acids, for example lactic acid, or less desirably, glycolic acid, included in a valerian extract formulation provides a valuable anti-wrinkle formulation which employs natural biological active ingredients and is an effective treatment for both fine, superficial wrinkles and deep wrinkles. The alpha hydroxy acid or acids should preferably be present in a proportion of from about 0.5 to about 6 percent by weight, more preferably from about 1 to about 3 percent, although a proportion of from about 0.1 to about 10.0 weight percent could be used. Alternatively, tretinoin or an equivalent such as vitamin a palmitate can be used in an appropriate (lower) proportion, for example from about 0.01 to about 0.5 percent by weight, preferably about 0.05 to about 0.3 percent.

Other herbs or herbal extracts having calming or relaxant properties can also be included, in addition to, or if adequately effective, in place of, valerian root extract. Some examples of such herbs are passion flower and comfrey, believed by the inventor hereof to be used by veterinarians to calm animals. They can be used in an equivalent manner and quantity to valerian root extract, or in other ways known to those skilled in the art.

Application Rates and Frequencies

Suitable rates for topical application of the herbal relaxant actives used in the novel aged skin treatment compositions described herein can range from about 0.01 to 0.5 mg of active acid ingredients per square centimeter of skin, with a range of from 0.05 to 0.2 mg/cm$^2$ being preferred. Liquid phase cosmetics are generally applied at rates of about 2–3 mg/cm$^2$. With an active ingredient proportion of about 0.15 to about 30 weight percent, this gives a possible rate of application of active ingredients of from about 0.003 mg/cm$^2$ to 0.9 mg/cm$^2$. A preferred range is from about 0.01 to 0.5 gm/cm$^2$, with a range of from 0.05 to 0.2 mg/cm$^2$ active ingredient per unit skin area being more preferred.

This dosage is applied to whatever skin area requires treatment, preferably once or twice a day. More frequent applications of three or four times a day are likely to be wasteful of product without providing additional benefits, whereas less frequent applications, notably once a day, result in reduced efficacy. Additional applications may be occasionally be made after washing, bathing or swimming, up to a maximum of about six times a day.

EXAMPLE 2

Herbal Gel for Treating Wrinkles

A skin care product formulated as a topical gel is prepared from the following ingredients in the proportions indicated, being by weight based upon the total weight of the composition, by methods known to those skilled in the art:

Water 64.0%

Propylene glycol 10.0%

Carbopol 940 (trademark, Goodrich) carbomer 0.2%

Valerian root extract 10.0%

Glycerine 10.0%

Hispagel* 5.0%

Phenoxyethanol 0.8%

*Polymethylmethacrylate thickener (Centerchem, Inc.)

The resultant topical gel is an esthetically pleasing clear cosmetic composition that is easily applied to the face, neck, hands or any other desired body surface to be treated, with little or no preceptible odor or color attributable to the valerian root extract, and with good shelf life. It is used in the clinical tests described below.

Test Methods

Pursuant to the invention, the following methods can be used to evaluate the visible signs of aging induced by stress-induced tension and were used in the clinical test reported below to evaluate the effects on the appearance of aged skin of an orally ingested valerian tea both alone and when combined with topical application of treatment compositions containing a herbal relaxant, namely, valerian root extract.

Evaluations of skin characteristics were made by trained technicians and were clinically graded on a pre-defined scale.

Wrinkle counts. Wrinkle counts were determined according to the method of Packman wherein wrinkles are enumerated around the eyes and lip area and summed. Wrinkles are distinguished from fine lines which are not included in wrinkle counts, see Packman E. W. and Gams E. H., *Journal of the Society for Cosmetic Chemistry*, volume 29, pages 79–90 (1978). Pursuant to Packman, fine lines are superficial intrusions into the stratum corneum and upper epidermis, generally less than about 0.1 mm deep, and can usually be eliminated, at least visually, by hydration. Accordingly, wrinkle counts are reported herein do not include such fine lines, but do include deeper intrusions into the epidermis and dermis to an extent greater than about 1 mm, which are not easily removed.

Skin texture. Skin texture was evaluated on a 0–4 point scale, as follows:

0 Smooth.
1 Dry, slightly rough.
2 Flakiness, lines.
4 Uplifted clumps, lines, coarse.

Skin color. Skin color was evaluated globally, i.e. over substantial or complete relevant body areas, with respect to evenness using visual judgment. Intensity or lightness was evaluated as an L-value determined by a colorimeter, in this case a Minolta chroma Meter, Minolta Camera Co. Ltd.

Acne lesion count. Acne was counted globally, meaning a full face count, was made, including inflamed and non-inflamed lesions or comedones, using a magnifying glass to examine subjects without makeup.

Puffiness. Puffiness was graded tactilely and visually by inspecting the sub-orbital eye area. As a check, the area was probed with a blunt-tipped, 1 mm. instrument to examine its indentation properties and ensure that the examined eye was really puffy, not just structurally unusual.

Clinical Determinations of Efficacy

The results of clinical tests designed to relieve the visible signs of aging induced by stress-related muscle tension, as well as controls, are reported in Table 1 below. These tests employed ingestion of teas and topical application of skin care supplements and were performed on groups of women clinically determined to be stressed with groups of "unstressed" women serving as controls. Noting that we are all subject to stress, the term "unstressed", as used herein, is intended to refer to a condition relatively free from clinical indications of excess stress, especially muscle tension, such a condition being obtained by suitable medication or lifestyle changes.

Comparative evaluations of visual facial characteristics, namely wrinkles, skin texture, skin color, acne lesions, and puffiness were made according to the test methods described above.

Tests 1a) and 1b) were run as comparatives to establish the validity of the selected visual evaluation tests as quantifiers of stress-related skin effects.

Test 1a) A test group of 20 women clinically determined to be under stress and not taking any medication for at least two weeks yielded the clinical scores reported in line a). The subjects had a history of stress and were diagnosed subjectively, and professionally, as being under significant stress, from the burdens of motherhood, taxing jobs, martial problems, long commutes or financial worries or combination of these factors. All had been prescribed commercial drugs to relieve stress or tension recently prior to Test 1a).

Test 1b) When the group of 20 women evaluated in Test 1a) was clinically determined to have been stress-free for a period of at least two weeks as a result of lifestyle changes or taking prescribed medications, they were re-evaluated yielding the clinical scores reported in line b).

A second group of 20 subjects was then divided into two groups to determine the efficacy respectively of a relaxant herbal tea and of a topical treatment composition incorporating a relaxant herbal agent, Tests 1c)–f).

Test 1c) The figures reported are the averaged results from Test 1b) for the ten individuals selected for the 1st group of 10 women.

Test 1d) The first group of 10 women whose untreated, unstressed results are reported in Test 1c) was provided with the ingredients for making what was in fact a placebo, decaffeinated tea for drinking at least twice a day for two weeks. They were re-evaluated and the results are reported in line d) of Table 1.

Test 1e) The figures reported are the averaged results from Test 1b) for the ten individuals selected for the 2nd group of 10 women.

Test 1f) The 2nd group of 10 women whose untreated, unstressed results are reported in Test 1e) was provided with the ingredients for making a valerian tea, according to Example 1, above, for drinking at least twice a day for two weeks. They were re-evaluated and the results are reported in line f) of Table 1.

For tests 1g) and 1h) a separate group of 10 subjects was used. Each subject refrained from using any sleeping pill, herbal or chemical relaxant, or prescription medication during the course of a 4-week study.

Test 1g) Each of the 3rd group of 10 subjects was clinically evaluated at the beginning of the 4-week study and the results are reported in line 1g) of Table 1.

Test 1h) Each of the 3rd group of 10 subjects applied a study treatment comprising drinking valerian tea prepared as described above, at least twice a day, or more often if they wished, combined with topically applying a skin care product containing a herbal relaxant, in this case valerian root extract, to the face at least twice a day. Each subject was clinically evaluated after 4 weeks treatment and the results are reported in line 1h).

TABLE I

Clinical Test Results
Studies on the visible cutaneous effects of ingested and topical valerian,
versus controls on stressed and unstressed female subjects.

| DESCRIPTION OF TEST GROUP | WRINKLES | SKIN TEXTURE | SKIN COLOR | ACNE LESIONS | PUFFINESS |
|---|---|---|---|---|---|
| a) Group of 20 (stressed) | 17.6 | 2.3 | 1.1 | 2.7 | 3.5 |
| b) Group of 20 (unstressed) | 13.4 | 3.4 | 2.5 | 1.7 | 3.2 |
| c) 1st Group of 10 (stressed) + | 17.2 | 2.2 | 1.1 | 2.7 | 3.2 |
| d) decaffeinated tea (control) | 14.7 | 2.4 | 1.5 | 2.4 | 3.2 |
| e) 2nd Group of 10 (stressed) + | 17.9 | 2.1 | 1.1 | 2.7 | 3.2 |
| f) valerian root tea | 12.6 | 3.6 | 2.7 | 1.8 | 3.1 |
| g) 3rd Group of 10 (stressed) + | 16.2 | 2.3 | 1.1 | 2.7 | 3.2 |
| h) valerian tea + topical gel | 7.5 | 4.2 | 3.7 | 0.8 | 1.2 |

Comparing the unstressed appearance reported in line b) with the stressed skin appearance reported in line a) the quantified skin appearance tests employed revealed significant improvements in visual skin characteristics associated with relief of stress. Wrinkles were modestly reduced; skin texture improved; skin color improved; acne lesions were reduced and there was a slight reduction in puffiness. These results established the validity of the tests as an experimental basis for evaluating various therapies for their effects upon skin appearance, and suggest that relief of stress may be effective in improving the appearance of wrinkled skin.

A comparison of the control results of line d) with those of line c) for the untreated first group of 10 here shows that the results obtained by the placebo, decaffeinated tea, treatment are quite modest and are inferior to results obtained in line b) by conventional stress-avoidance and drug therapies.

In contrast, the group taking valerian root tea, line f) show a marked improvement which is better is several respects, wrinkle count, skin texture, and skin color, than the results provided by conventional anti-stress treatments, as reported in line b). Nor do these favorable results appear to be due to plumping of the skin via hydration, because there is no increase in measured puffiness.

The valerian root tea treatment had a positive effect on the skin. The results obtained with both a valerian root tea treatment and a topically applied valerian root extract gel as reported in line h), when compared with the base data reported in line g) showed a marked or dramatic effect on skin appearance with every one of the five tested characteristics attaining superior values to those produced by the conventional stress treatment of line b). Also, comparing line h), valerian tea, with line f), valerian tea plus topical application of a valerian gel, show an additional significant improvement in all appearance characteristics, and especially in a reduced wrinkle count, which improvement may be attributed to the use of valerian gel as an additional treatment to the drinking of valerian tea. Again, these positive results do not appear to be due to plumping of the skin via hydration, because there is no increase in measured puffiness; on the contrary, puffiness is significantly decreased.

The favorable results obtained by valerian root tea, as observed clinically, were confirmed subjectively when the subjects of the first and second groups of ten were asked to rate the degree of improvement of their skin obtained by the test treatment on an arbitrary scale ranging from 0 for no improvement to 4 for dramatic improvement. The results of these subjective evaluations are reported in Table 2 below.

TABLE 2

Subjective Evaluations

| DESCRIPTION OF TEST GROUP | RATING OF EFFECTS |
|---|---|
| Control group subjects of Test d) | 1.1 |
| Valerian root tea subjects of Test e) | 3.2 |

The Table 2 data show that the control group drinking decaffeinated tea reported a modest improvement whereas those drinking valerian root tea averaged a quite significant improvement, in their own judgment.

Conclusions

These data support the conclusion that the drinking of a relaxing herbal tea to reduce stress can have a therapeutic effect on the appearance of the skin. The data also support the conclusion that the use of valerian root extracts as a relaxant herbal drink and in a topical skin care product can have marked effects on improving the appearance of the skin, especially with respect to reducing wrinkles and puffiness.

Further Suitable Vehicles

Any cosmetically acceptable vehicles customarily employed for delivering skin treatments can be employed in formulating topical treatments pursuant to the practice of this invention, so long as the vehicles used to not interfere with the action of the active herbal agents.

If desired, the active ingredients can be formulated in a cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol. While a number of lower aliphatic alcohols, both monohydric and polyhydric can be used, ethanol and propanol are the most preferred choices.

Many additives and supplemental materials are known to the art as being useful for incorporation in such vehicles, for example, glycerine up to about 5 percent, preferably 1 to 2 percent is useful as a humectant to counteract the drying effect of the alcohol and to improve the feel of the tonic. Stabilizers, fragrances and colorants are examples of other such additives.

Other suitable vehicles include a hydrophobic dispersion of from about 5 to about 60 weight percent of a hydrophobic fluid dispersed in an aqueous medium, and include water.

If desired, pH adjustment to a preferred range, for example, pH 3.5–5.0 for an acidic treatment, can be effective with from 0.1 to 10 weight percent of an alkaline medium, for example aqueous sodium hydroxide, arginine or triethanolamine (TEA), and if desired may also be buffered, for example with from about 0.1 to 10 weight percent, preferably about 1 or 2 percent of a suitable buffers such as a TRIS (trimethylolaminomethane) buffers or phosphate buffer.

Theoretical Considerations

While the invention is not limited by any particular theory, but only by the appended claims, it may help an understanding of the nature of the invention to consider some relevant conceptual aspects. Clearly, the condition of skin suffering defects such as deep wrinkles, fine lines and so on, is improved by countering stress. Removal of adverse lifestyle factors or prescription drugs, though apparently effective in countering stress, provides only modest improvements in skin appearance, especially with regard to deep wrinkles. Ingestion of a relaxant herbal tea provides significantly greater improvements which are not displayed by a placebo non-relaxant tea and the improvement is greatly enhanced by topical application of a cosmetic composition containing the herbal relaxant agent.

These results can be better understood in the light of the general herbal and holistic precept that the natural complexity of botanical materials can yield biological benefits not obtainable by an individual active agent or a simple mixture of active agents. In traditional scientific terms this phenomenon may be explained by postulating that the complex constitution of botanical materials conceals one or more additional active agents that have yet to be identified and characterized. Herbalists, however, would disfavor explanations based on active agent hypotheses, preferring to look at the overall effects of a particular plant extract or native source. This alternative viewpoint depends on the idea that the multifarious ingredients of effective botanicals are responsible for a variety of subtle biological effects which complement one another, leading to an outcome which is greater than the sum of the effects of the individual components.

Doubtless, these ideas will be better understood in the future. Toward the thrust of these teachings the herbal relaxant agents employed in the practice of the present invention should retain significant natural complexity. Thus, an individual agent may be solvent extracted to enhance its potency and may be somewhat refined to remove clearly undesirable components such as noxious aromatics or toxics, but are preferably not fractionated. Any fractionation to remove undesirables should select for use in the invention a broadband fraction that retains a nub of the natural complexity of the botanical source material.

The skin system is extremely complex and many of its growth and repair mechanisms are only poorly understood. Clearly the skin system responds favorably to relaxation and the relief of stress, whether systemically or locally applied, yet, surprisingly, the herbal teas of the present invention are more effective than commercial drugs. It is also possible that herbal relaxant agents include in their complexity agents that stimulate or foster the skin's natural growth processes, encouraging a healthy skin structure and a clearing of unsightly conditions.

INDUSTRIAL APPLICABILITY

The present invention is particularly suitable for application in the cosmetics and beauty treatment industries providing new methods of treatment that may be used in clinics or spas and providing new compositions which may be commercially marketed in these industries.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A herbal treatment for stress-related deep wrinkles comprising chronic oral administration for at least two weeks of a beverage containing an effective amount of a valerian root extract sufficient to provide a desired reduction in the appearance of said deep wrinkles.

2. A herbal treatment according to claim 1 wherein said chronic oral administration is effected by an individual under stress drinking at least two aliquots per day of at least about 100 ml. valerian tea at least twice daily for at least four weeks until a desired improvement in the deep wrinkles is obtained, each said aliquot of valerian tea containing an aqueous extract of from about 0.1 to about 2 g. dry weight of powdered valerian root.

3. A herbal treatment according to claim 1 further comprising topical application to the wrinkles to be reduced of a topical composition comprising an effective amount of an aqueous valerian extract.

4. A herbal treatment according to claim 2 further comprising topical application to the wrinkles to be reduced of a topical composition comprising an effective amount of an aqueous valerian extract.

5. A herbal skin treatment for reducing visible signs of aging induced by stress-related tension comprising administering a skin treatment composition containing an effective quantity of a biologically active relaxant herbal agent, to a subject having visually apparent aged skin, wherein the herbal agent comprises an aqueous extract of a dry biological source material selected from the group of herbs consisting of valerian, passion flower, mullein, skullcap, lady's slipper, magnolia, arrach and comfrey, at a concentration whereby, taking into account the quantity of herbal agent in the skin treatment comprising, the proportion of source material to skin treatment composition is at least 0.5 percent by weight to provide a desired reduction in the appearance of said deep wrinkles.

6. A herbal skin treatment according to claim 5 wherein said treatment is administered daily for at least two weeks to a subject suffering from stress.

7. A herbal treatment according to claim 5 wherein said herbal agent has relaxant properties, is substantially non-toxic, can be satisfactorily formulated for administration and is selected from the group of herbal agents having muscle-relaxant, anti-hypertensive, anti-convulsant or tranquilizing properties.

8. A herbal skin treatment according to claim 5 comprising an orally ingestible potable tea or hot water infusion of a plant material, or concentrated extract of plant material providing a suitable source of the active herbal agent.

9. A herbal skin treatment according to claim 5 comprising a cosmetic composition formulated with cosmetic excipients for topical application.

10. A herbal skin treatment according to claim 5 comprising a combination of the ingestion of a herbal tea containing an effective amount of a first relaxant herbal agent and the daily topical application of a cosmetic composition also containing an effective amount of an active herbal relaxant agent.

11. A herbal method of reducing the appearance of stress-related deep wrinkles and improving skin texture of aged skin comprising:
   a) drinking a tea containing an effective proportion of a relaxant herbal extract; and
   b) applying, to the aged skin, a topical cosmetic composition containing an effective proportion of a relaxant herbal extract, both said herbal extract selected from the group consisting of valerian, passion flower, mullein, skullcap, lady's slipper, magnolia, arrach and comfrey;

wherein the tea drinking and topical application are performed at least once daily for at least two weeks and until a desired improvement in skin appearance is obtained.

12. A herbal, topicallally applicable cosmetic composition for reducing visible signs of aging induced by stress-related tension comprising an effective proportion of a valerian root extract formulated with cosmetic excipients suitable for topical application wherein the herbal agent comprises an aqueous extract of a dry biological source material at a concentration whereby, taking into account the quantity of herbal agent in the skin treatment composition, the proportion of source material to skin treatment composition is at least 0.5 percent by weight.

13. A herbal treatment according to claim 2 wherein said valerian tea consists essentially of an aqueous extract of powdered valerian root alone in water alone, or in a mixed solvent consisting of water and an ingestible water-miscible alcohol or glycol or both.

14. A herbal skin treatment according to claim 8 wherein the herbal agent consists essentially of an aqueous extract of the individual powdered herb alone in water alone, or in a mixed solvent consisting of water and an ingestible water-miscible alcohol or glycol or both.

15. A herbal skin treatment for reducing visible signs of aging induced by stress-related tension comprising administering a skin treatment composition consisting essentially of an effective quantity of a biologically active relaxant herbal agent, selected from the group consisting of valerian, passion flower, mullein, skillcap, lady's slipper, magnolia, arrach and comfrey, to a subject having visually apparent aged skin to provide a desired reduction in the appearance of said deep wrinkles.

16. A herbal skin treatment according to claim 15 wherein said treatment is administered daily for at least two weeks and said herbal agent has relaxant properties, is substantially non-toxic, can be satisfactorily formulated for administration and is selected from the group of herbal agents having muscle-relaxant, anti-hypertensive, anti-convulsant or tranquilizing properties.

17. A herbal skin treatment according to claim 15 comprising a cosmetic composition formulated with cosmetic excipients for topical application and wherein the active herbal relaxant agent in both the tea and the cosmetic composition is an extract of a herb selected from the group consisting of valerian, passion flower, mullein, skullcap, lady's slipper, magnolia, arrach and comfrey.

* * * * *